(12) United States Patent
O'Sullivan et al.

(10) Patent No.: US 10,617,430 B2
(45) Date of Patent: Apr. 14, 2020

(54) SURGICAL BUR WITH A SINGLE CUTTING FLUTE

(71) Applicant: Stryker European Holdings I, LLC, Kalamazoo, MI (US)

(72) Inventors: Denis O'Sullivan, Cloughoulamore (IE); Sinéad Hughes, Piperhill (IE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 555 days.

(21) Appl. No.: 15/429,364

(22) Filed: Feb. 10, 2017

(65) Prior Publication Data

US 2017/0150974 A1    Jun. 1, 2017

Related U.S. Application Data

(63) Continuation of application No. PCT/US2015/045044, filed on Aug. 13, 2015.

(60) Provisional application No. 62/037,231, filed on Aug. 14, 2014.

(51) Int. Cl.
*A61B 17/16* (2006.01)
*B23C 5/10* (2006.01)

(52) U.S. Cl.
CPC ............ *A61B 17/1615* (2013.01); *B23C 5/10* (2013.01); *B23C 2210/084* (2013.01); *B23C 2210/201* (2013.01)

(58) Field of Classification Search
CPC .. A61B 17/16; A61B 17/1615; A61B 17/1604
See application file for complete search history.

(56) References Cited

U.S. PATENT DOCUMENTS

| | | | |
|---|---|---|---|
| 2,818,753 A | 1/1958 | Leggett | |
| 3,633,583 A | 1/1972 | Fishbein | |
| 3,732,858 A | 5/1973 | Banko | |
| 3,836,278 A | 9/1974 | McInnes | |
| 4,512,344 A | 4/1985 | Barber | |
| 4,943,236 A * | 7/1990 | Linkow | A61B 17/1615 408/59 |
| 5,007,917 A | 4/1991 | Evans | |
| 5,857,995 A | 1/1999 | Thomas et al. | |
| 5,888,200 A | 3/1999 | Walen | |
| 6,562,055 B2 | 5/2003 | Walen | |
| 8,460,298 B2 | 6/2013 | O'Donoghue | |

(Continued)

FOREIGN PATENT DOCUMENTS

CA    2615969 A1    1/2007
CN    102510738 A    6/2012

(Continued)

OTHER PUBLICATIONS

EPO, "ISA Search Report and Written Opinion for PCT/US2015/045044", dated Dec. 2015.
English language abstract and machine-assisted English translation for DE 10 2012 110 253 extracted from espacenet.com database on Sep. 26, 2018, 136 pages.

(Continued)

*Primary Examiner* — Andrew Yang
(74) *Attorney, Agent, or Firm* — Howard & Howard Attorneys PLLC (57) ABSTRACT

A surgical bur with a head that defined a single flute. The flute has a rake surface with a cutting edge and an opposed recess edge. The cutting edge is spaced further from axis of shaft of the bur than the recess edge. The rake surface is often, but not always, planar.

23 Claims, 9 Drawing Sheets

(56) References Cited

U.S. PATENT DOCUMENTS

| | | |
|---|---|---|
| 8,529,568 B2 | 9/2013 | Bouadi |
| 8,657,537 B2 | 2/2014 | Delacretaz |
| 9,179,923 B2 | 11/2015 | Gubellini et al. |
| 2002/0107521 A1 | 8/2002 | Petersen et al. |
| 2007/0276395 A1 | 11/2007 | Burn |
| 2009/0022561 A1 | 1/2009 | Winebrenner |
| 2010/0030282 A1 | 2/2010 | Ciccone et al. |
| 2010/0063524 A1 | 3/2010 | McCombs |
| 2012/0158208 A1 | 6/2012 | Kawamoto et al. |
| 2013/0274779 A1 | 10/2013 | Kulas et al. |

FOREIGN PATENT DOCUMENTS

| | | | |
|---|---|---|---|
| DE | 102012110253 | A1 | 4/2014 |
| JP | S6078213 | U | 5/1985 |
| JP | 2000515395 | A | 11/2000 |
| JP | 2013154428 | A | 8/2013 |
| WO | 9721392 | A1 | 6/1997 |
| WO | 2007010389 | A1 | 1/2007 |
| WO | 2007077535 | A2 | 7/2007 |
| WO | 2008061711 | A2 | 5/2008 |
| WO | 2011023381 | A1 | 3/2011 |
| WO | 2013158469 | A1 | 10/2013 |

OTHER PUBLICATIONS

Chinese Office Action and Translation for Application No. 2015800504788 dated Jul. 4, 2018, 14 pages.

English language abstract for CN 102510738 extracted from espacenet.com database on Dec. 7, 2017, 2 pages.

Brilhault, MD, PhD, Jean, "Single Medial Approach to Modified Double Arthrodesis in Rigid Flatfoot with Lateral Deficient Skin", Foot & Ankle International, 2009, pp. 21-26.

Brown, Austin, "A Simple Method of Fusion of the Subtalar Joint in Children", The Journal of Bone and Joint Surgery, vol. 50B, No. 2, May 1968, pp. 369-371.

Gougoulias, M.D., Nikolaos et al., "Arthroscopic Ankle Arthrodesis", Foot & Ankle International, 2007, pp. 695-706.

Maskill, DPM, Michael P. et al., "Triple Arthrodesis for the Adult-Acquired Flatfoot Deformity", Clin Podiatr Med Surg 24, 2007, pp. 765-778.

Machine-assisted English language translation for JPS 60-78213 extracted from espacenet.com database on Apr. 24, 2019, 3 pages.

English language abstract for JP 2000-515395 extracted from espacenet.com database on Apr. 24, 2019, 2 pages.

English language abstract and machine-assisted English language translation for JP 2013-544428 extracted from espacenet.com database on Apr. 24, 2019, 26 pages.

* cited by examiner

SURGICAL BUR WITH A SINGLE CUTTING FLUTE

FIELD OF THE INVENTION

The present invention relates generally to surgical burs. More specifically, the present invention relates to bur with a head, including a cutting flute designed to facilitate the flow of cut material away from the cutting flute.

BACKGROUND OF THE INVENTION

A cutting accessory is an implement typically removably attached to a powered surgical handpiece to perform a surgical procedure. One cutting accessory used to perform a surgical procedure is a bur. A bur generally comprises a head formed from rigid material, typically metal, shaped to have a number of flutes. The flutes are formed to define cutting edges. The flutes, including the cutting edges are shaped to cut tissue, such as bone or cartilage. A shaft extends proximally from the head. A proximal end of the shaft often has a feature that facilitates locking the shaft to the powered handpiece. Actuation of the handpiece results in rotation of the bur. During a surgical procedure, the head of the bur is placed against a surgical site where a section of tissue is to be removed. The rotating cutting edges excise tissue away from the surgical site. Burs of various shapes and sizes are used in procedures such as orthopedic surgery, neurological and spinal surgery, ear nose and throat surgery and in other surgical procedures to selectively remove a section of tissue.

Many burs work well for the general purpose of removing tissue. Nevertheless, burs have not proven particularly efficient devices for removing tissue in some procedures. For example, it can sometimes be difficult to employ a bur to remove cartilage around a small joint such as the ankle or wrist. This is because cartilage, in comparison to other types of tissue, contains a large percentage by volume of water. When cartilage is cut from tissue, the water component of the cartilage causes the cartilage to adhere to the cutting device. When the cutting device is a bur, the cartilage tends to adhere to surfaces of the flutes. Tissue also collects in the spaces between the adjacent flutes. This cut tissue effectively becomes a debris mass that is pushed around by the flutes. The presence of this debris mass reduces the ability of the cutting flutes to perform their function, to cut more tissue. Further, the debris mass is inherently pushed against the uncut tissue. This moving matter against stationary matter contact results in frictional heating of the debris and the uncut tissue. This heating can damage tissue not intended for removal.

Given the less than efficient cutting of cartilage with a bur, many practitioners, when performing this type of procedure tend to use surgical instruments other than burs to remove this tissue. These instruments tend to be manually operated instruments such as curettes, rongeurs and osteotomes. These instruments are useful for removing soft tissue like cartilage. Given that they are manually operated they are less efficient to use than powered tools such as burs.

SUMMARY OF THE INVENTION

This invention is directed to a new and useful surgical bur. The bur of this efficient is especially suited to efficiently remove tissue that has a tendency to adhere to the instrument used to remove the tissue.

The bur of this invention includes an elongated shaft. A longitudinal axis extends proximally to distally through the shaft. The shaft has features that facilitate the releasable coupling of the shaft to powered handpiece capable of rotating the shaft around the longitudinal axis. A head extends forward from the distal end of the shaft. The head has two opposed surfaces; a rake surface and a clearance surface. The head has a longitudinal axis that extends proximally to distally through the head and that is located between the rake and clearance surfaces.

The rake surface at least partially forms two opposed edges that extend longitudinally along the head on opposed sides of the rake surface. One of these surfaces is a cutting edge, the opposed edge is a recess edge. In some versions of the invention the bur is formed so that the cutting edge defined by the rake surface is spaced radially outwardly further away from the longitudinal axis of the shaft than the distance the recess edge is spaced from the same axis.

In some versions of the invention, rake and clearance surfaces are spaced apart from each other. In these versions of the invention, on one side of the head a relief surface extends between the rake and clearance surfaces. On the other side of the head, a recess surface extends between the clearance surface and the rake surface. The interface of the rake surface and the relief surface defines the cutting edge. The interface between the recess surface and the rake surface defines the recess edge.

In some sub versions of the above described version of the invention the rake and clearance surfaces are parallel.

In some versions of the invention, the bur is further formed so that the longitudinal axis through the shaft and the longitudinal axis through the head are not collinear. In some sub versions of this version of the invention, the head is further located relative to the shaft so the rake surface lies in plane through which the longitudinal axis of the shaft extends. In some sub versions of this latter version of the invention, the cutting edge and the clearance edge of the flute may be equidistantly spaced apart from each other relative to the longitudinal axis of the shaft.

BRIEF DESCRIPTION OF THE DRAWINGS

The invention is pointed out with particularity in the claims. The above and further features and benefits of the invention are better understood from the following Detailed Description taken in conjunction with the accompanying drawings in which:

DETAILED DESCRIPTION

Figure 1:
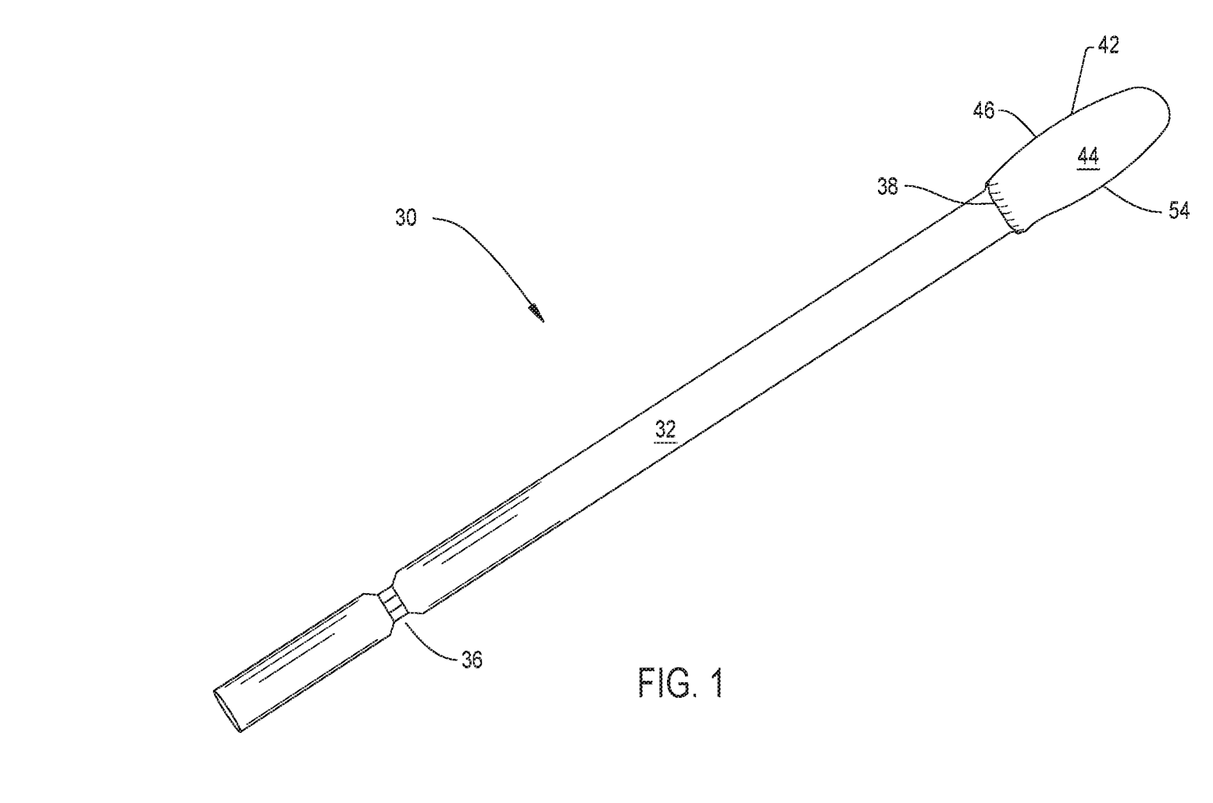
FIG. 1 is perspective view of a bur constructed in accordance with this invention.

As seen in FIG. 1, a surgical bur 30 constructed in accordance with this invention includes an elongated generally cylindrical shaft 32. A head 42 extends forward from the distal end of the shaft 32. (Here, "distal" is understood to mean away from the practitioner holding the handpiece to which the bur 30 is attached and towards the site to against the head 42 is applied. "Proximal" is understood to means towards the practitioner, away from the site against which bur head 42 is applied.) Shaft 32 has a longitudinal axis represented by dashed line 34 in FIG. 2.

Coupling features 36 are provided at the proximal end 24 of the shaft 32. The coupling features 36 are geometric features that facilitate the removable engagement of the bur 30 to a coupling assembly integral with a rotating shaft of a powered surgical handpiece or tool (not shown) with which the bur 30 is used. The illustrated coupling features 36 are surfaces that are recessed relative to the outer cylindrical shaft. These surfaces are described in U.S. Pat. No. 5,888, 200 MULTI-PURPOSE SURGICAL TOOL SYSTEM, incorporated herein by reference. Alternative coupling features are disclosed in U.S. Pat. Pub. No. 2010/0063524 A1 (WO 2010/028001 A2), the contents of which are also explicitly incorporated by reference. Other alternative geometries for the coupling features are illustrated in U.S. Pat. No. 6,562,055, CUTTING ATTACHMENT FOR A SURGICAL HANDPIECE DESIGNED TO BE SELECTIVELY COUPLED TO THE HANDPIECE, the contents of which are hereby explicitly incorporated by reference. It should be appreciated that these coupling feature geometries are exemplary, not limiting. The geometry of the coupling features 36 is not intended to limit the present invention. For example, a portion of the smooth walled shaft 32 itself may simply be dimensioned to be held to the handpiece by chuck jaws that are part of the handpiece coupling assembly.

Figure 5:
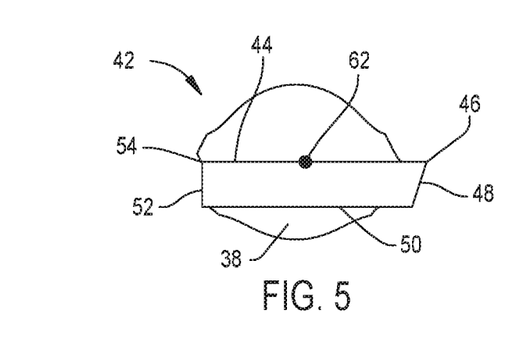
FIG. 5 is a plan view of the bur of FIG. 1 looking proximally from the distal end of the bur head.

Distally forward of shaft 32, bur head 42 has opposed parallel rake and clearance surfaces 44 and 50, respectively, seen in FIGS. 2-5. At one side of the head 42, a relief surface 48 extends between the rake surface 44 and the clearance surface 50. The edge between the rake surface 44 and the relief surface 48 is the cutting edge 46 of the head 42. In many versions of the invention, the head 42 is formed so that the angle between the rake surface 44 and relief surface 48 is such that, extending from the cutting edge 46, the relief surface extends inwardly back towards a line that extends from the shaft longitudinal axis 34. In FIG. 5 the extension of this axis 34 extends in and out of the Figure and is represented by point 62.

Bur head 42 is further formed so that, opposite the relief surface 48, a recess surface 52 extends between the rake surface 44 and clearance surface 50. The edge where the rake surface 44 and recess surface 52 meet is referred to as the recess edge 54. The proximal to distal longitudinally extending sides of the relief surface extend between, at one side, from the cutting edge 46 to, on the opposed side, the recess edge 54. Bur head 42 is further formed so that cutting edge 46 and recess edge 52 are not symmetrically located around the line that extends from the shaft longitudinal axis 34. Instead, bur head 42 is shaped so that, in planes perpendicular to the extension of the shaft longitudinal axis 34, cutting edge 46 is spaced a further distance from the extension of the axis 34 than the recess edge 52. In the version of the invention depicted by FIGS. 1-5, bur head 42 is formed so that cutting edge 46 and recess edge 52 are on opposed sides of the extension of the shaft longitudinal axis 34.

A neck 38 is the transition section of bur 30 between shaft 32 and head 42. Neck 38 has two face surfaces, not identified, that, extending distally forward curve inwardly. One of these surfaces curves inwardly to define the rake surface 44. The opposed neck surface curves inwardly to define the bur head clearance surface 50. The neck has two opposed side surfaces (not identified) that are convex in shape. Each side surface extends between one of the face surfaces. As the neck extends forward from the shaft 32 the neck side surfaces curve outwardly away from the shaft 32.

Bur head 44 is formed so that, extending distally from the neck 38, the relief surface 48 and, by extension the cutting edge 46, curves slightly outwardly away from the extension of the shaft longitudinal axis. At a location approximately one-half along the proximal to distal length of the bur head, the relief surface 48 starts to curve inwardly back toward the extension of the shaft longitudinal axis 34. On the opposed side of the head, recess surface 52 as the surface extends distally from the neck 38 initially has that curves inwardly, towards the extension of the shaft longitudinal axis 34. Where the recess edge 52 curves inwardly as a result of this curving of the recess surface is called out as section 53 of the recess edge in FIG. 2, At a location approximately one-sixth the length along the head, the recess surface 52 curves outwardly. Recess surface 50 then curves inwardly at approximately the same location along the shaft at which the clearance surface curves inwardly. Adjacent the top of the bur head, the radii of curvature of both the clearance and recess surfaces decrease. Relief surface 48 and recess surface 52 meet at the distal end tip of the bur head 42. The locations where surfaces 46 and 52 meet is also the most distal end of the bur 30.

Bur 30 of this invention is prepared for use the same way a conventional bur is prepared for use. The bur 30 is coupled to a handpiece (not illustrated) able to rotate the bur around the longitudinal axis that extends through shaft 32. To facilitate this coupling, the coupling members of the chuck integral with the handpiece engage the coupling features 36 of bur shaft 32. The bur is actuated by turning on the motor integral with the handpiece. This results in the rotation of the bur around the shaft longitudinal axis. In FIGS. 6A-6E this rotation would appear as counterclockwise rotation as represented by arrow 58 in FIG. 6A. In the procedure of FIGS. 6A-6E, the bur head is advanced laterally, generally to the side of the longitudinal axis of the bur shaft.

Figure 6A:
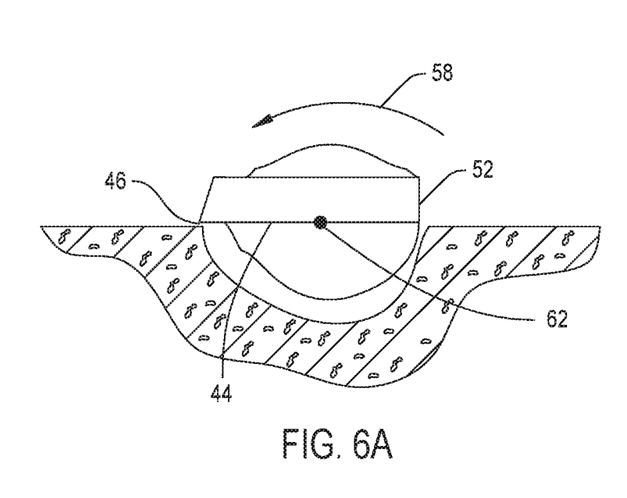
FIGS. 6A through 6E are a sequence of drawings that show the results of the cutting edge of the bur of this invention rotating against tissue when the bur head is pushed laterally against the tissue.
Figure 6B:
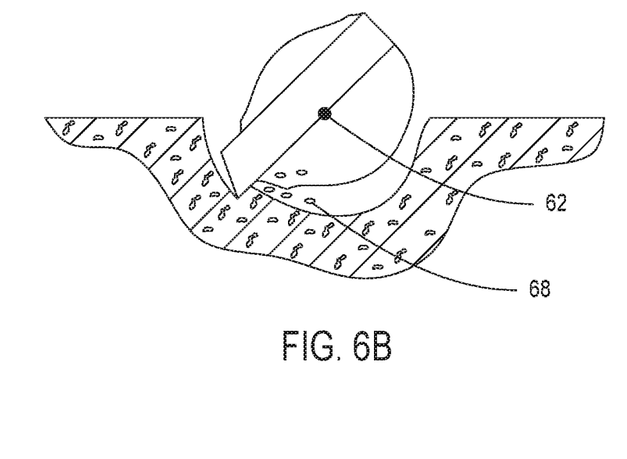
Figures 6C, 6D:
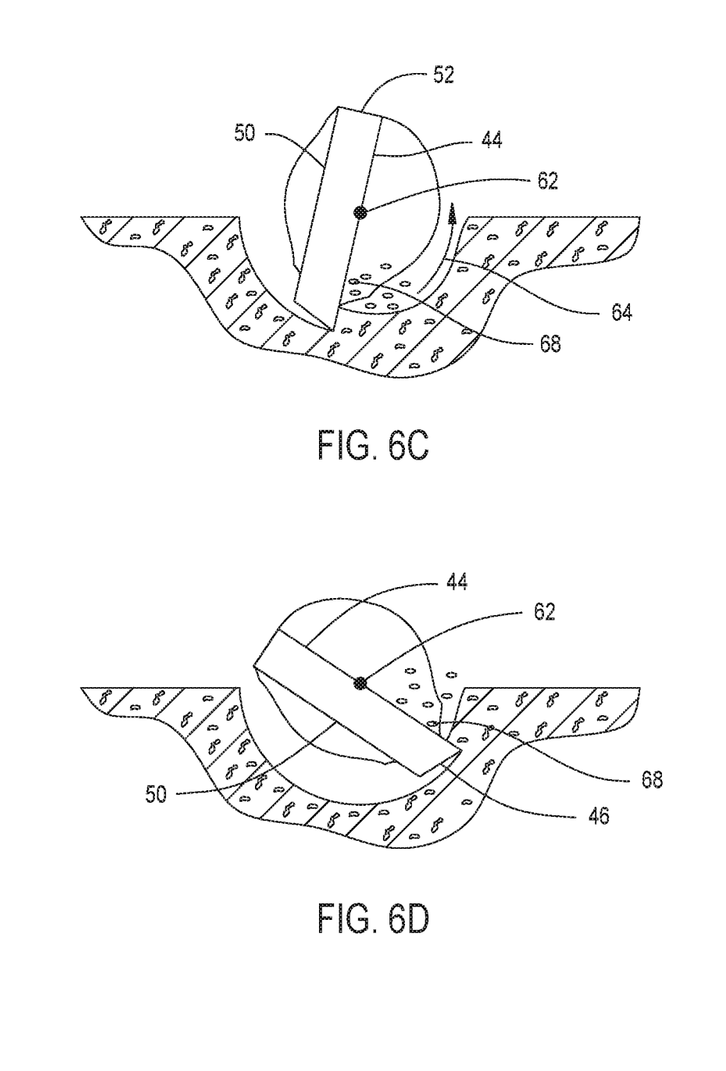

Bur 30 is used by pressing head 42 against the tissue to be removed. When the bur head is pressed against tissue, it is the rake surface 44 and cutting edge 46 that actually press against the tissue as seen in FIG. 6A. The cutting edge 46 and rake surface 44, shear, remove, the tissue against which this edge and surface are pressed. The removed tissue becomes debris 68 that are located in front of rotated with the rake surface as seen in FIG. 6B. The continued rotation of the bur head results in the continued removal of the tissue and the inherent increase in the volume of debris. In this invention, owing to planar nature of rake surface 44 the debris have a relatively unimpeded path away from the portion of the rake surface 44 defining the cutting edge 46. In actuality, there are two flow paths. A first one of these flow paths is the rotational flow path towards and then away from the outer surface of the tissue being cut. This flow path is represented by arrow 64 in FIG. 6C. The second flow path is longitudinally along the planar face of the rake surface 44. In FIG. 6C this is a flow path into the drawing, towards the bur shaft 32. The presence of two debris paths reduces the build up of debris adjacent the cutting edge 46 and the undesirable effects of such build up.

Figure 6E:
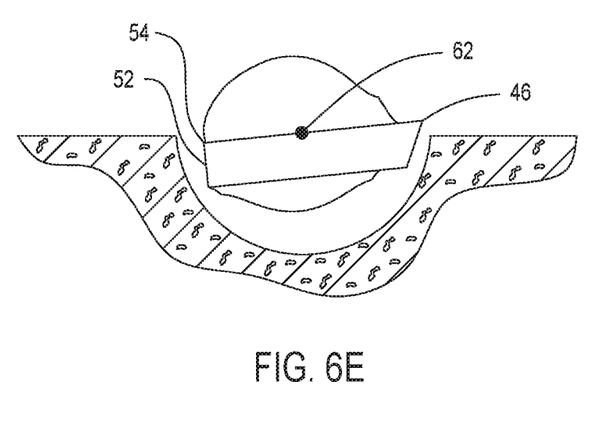

In the next phase of bur rotation, the cutting edge rotates away from the surface of the tissue being removed represented sequentially by FIGS. 6D and 6E. Simultaneously, the recess edge 54 and recess surface 52 rotate towards the surface of the tissue. However, owing to the relative position of the recess edge 54 and the cutting edge 46 to the axis of rotation, the shaft longitudinal axis, as seen in FIG. 6E, the recess edge 54 does not strike the tissue. In the Figures, this gap is enlarged for purposes of illustration. Instead, first the recess surface 52 and then the recess edge 54 rotate above the tissue. Thus, when this portion of the bur head rotate towards the tissue this portion of the bur head 42 is not exposed to the mechanical shock, the mechanical resistance, of the recess edge striking the tissue. The elimination of this shock results in a like reduction of the extent to which this shock induces undesirable back and forth vibration of the bur head.

Figure 7:
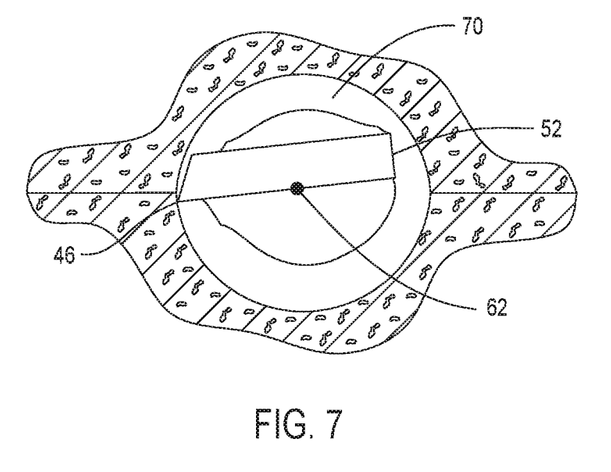
FIG. 7 is a partial cross sectional view showing the bur of this invention when the bur is advanced longitudinally to form a bore a hole that extends inwardly from the surface of tissue.

Further, it should be understood that the bur of this invention may sometimes be used to drill a hole like void 70 as seen in FIG. 7. In the type of procedure, the bur head is advanced longitudinally, at least generally distally along the longitudinal axis of the shaft. Tissue is not completely surrounding this void may surround the void by an arc that subtends at least 180°. In this type of procedure, the large side opening through which the cut debris can be discharged away from the remaining tissue as seen in FIGS. 6A-6E 6C may not be present or be substantially reduced in size. In this event debris are still able to flow essentially unimpeded along the longitudinal path towards the bur shaft.

Bur 30 of this invention is a useful tool for removing tissue that has a tendency to adhere to conventional burs while minimizing the exposure of the bur head 42 to mechanical shock that can foster the unwanted vibrations of the bur.

The reduction in debris around the cutting edge of this invention is believed to do more than reduce the extent to which these debris reduce cutting efficiency and reduce the unwanted heating of tissue. It is believed that the rapid ejection of the debris away from the cutting edge reduces the extent to which the debris, if otherwise present, reduce the ability of the cutting edge to, along the length of the edge smoothly shear, remove tissue. This increase in the ability of the cutting edge to remove tissue along a relatively linear bur-against-tissue line increases the smoothness of the hole cut by the bur. Here this smoothness is understood to mean both the consistency of the diameter of the hole and the minimization of in irregularities on the surface of the tissue that remaining after the cutting.

A further feature of the bur of this invention is that extending proximally from the distal end of the bur head 42 both the relief surface 48 and recess surface 52 curve outwardly. This feature of the bur of this invention allows the bur to be used as drill. In other words, the bur can be used to form a bore or a void that extends inwardly from the surface of the tissue along a line that is an extension of the shaft longitudinal axis. Thus bur 30 of this invention can be used to remove tissue by pressing the bur sideways, radially away from the shaft longitudinal axis, an linearly, along the shaft longitudinal axis.

The above is directed to one specific version of the bur of this invention. Alternative burs of this invention may have features different from what has been described.

For example, in the described version of the invention, the bur head 42 is formed so that the rake surface rake angle is 0°. This means that, as the bur head rotates, the angle between the rake surface 44 and the tangent of the circle around which the rake edge rotates is 90°. In alternative versions of the invention, the bur head may be formed so that the rake angle is either positive or negative. In these versions of the invention, the rake surface 44 therefore may not be completely planar along the whole of the surface 44.

In the described version of the invention, the rake surface 44 and the clearance surface 50 are parallel along the length of the bur head 42. This feature of the invention provides the bur head with mechanical strength. However, in other versions of the invention these surfaces 44 and 50 may not always be parallel. Thus, in some versions of the invention, the distance across these surfaces may decrease extending proximally to distally towards the distal end of the head. In other versions of the invention, at least one of the surfaces, typically the clearance surface may have a non-planar shape. Typically, the surface would be non-planar because the planar portions of the surface are interrupted by outwardly protruding reinforcing ribs.

Also, in the described version of the invention, the difference in distance of the recess edge 54 to the shaft longitudinal axis relative to the distance the cutting edge is from the same axis is substantially constant along the length of the bur head. For example, for a bur head having an overall a length of the between 0.8 and 1 cm, this difference is typically between 0.2 and 0.5 mm. In alternative versions of the invention, this difference may not be constant along the length of the bur head 42. Thus in some versions of the invention this difference may vary. More particularly, this difference may decrease as the distance between the cutting edge 46 and the longitudinal axis.

Figure 8:
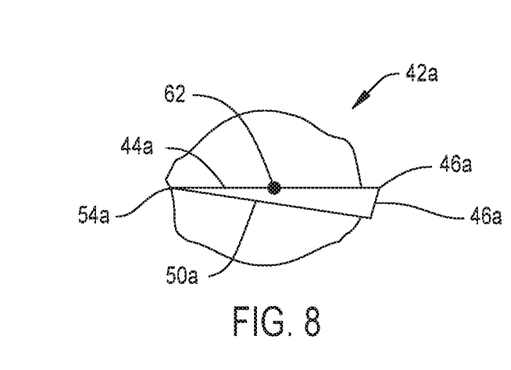
FIG. 8 is a plan view of a first alternative bur of this invention looking proximally from the distal end of the bur head.

Also, alternative shapes of the bur head are possible. FIG. 8 depicts a bur head 42a of this invention without a recess surface. In this version of the invention, as the clearance surface 50a extends inwardly from the relief surface 48a, the clearance surface tapers inwardly towards the rake surface 44a. At the end of the head opposite the relief surface 48a, the rake surface 44a and clearance surface 50a meet to define the recess edge 54a.

Figure 9:
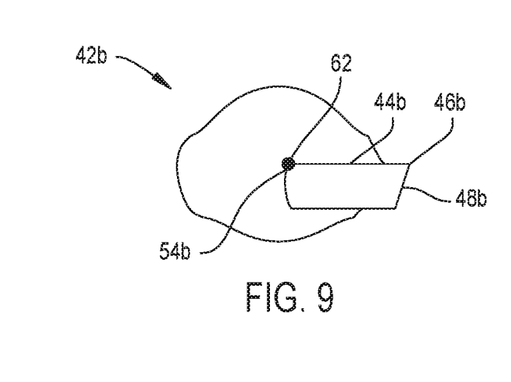
FIG. 9 is a plan view of a second alternative bur of this invention looking proximally from the distal end of the bur head.

The bur head 42b of FIG. 9 is formed so that the relief surface 44b does not extend appreciably beyond the longitudinal axis of the shaft 32. It should be understood that the bur head should generally extend to this location relative to the shaft 32. This is believed to be desirable to minimize asymmetric loading of the bur when the bur is rotated. One reason it is desirable to minimize this asymmetric loading is that such loading can induce chatter. Chatter is the unwanted back and forth vibration of the bur. These vibrations can occur at certain rotational frequencies. However, this design constraint may not be necessary in all versions of the invention.

FIG. 9 also illustrates that the recess surface 52b is curved in shape. While not illustrated, the rake surface may be similarly curved.

Figure 10:
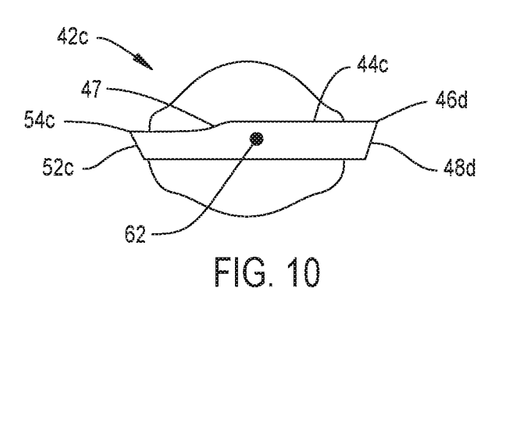
FIG. 10 is a plan view of a third alternative bur of this invention looking proximally from the distal end of the bur head.

FIG. 10 illustrates that there is no requirement that in all burs of this invention the, rake surface 44c lie in a plane through which the shaft longitudinal axes extends. The bur head 42c of FIG. 10 is further formed so that neither there is a curve 47 in the rake surface 44c. This curve form a recess in the section of the rake surface 44c adjacent the recess edge 54c. This recess serves as an additional void into which the debris that form during use of the bur can flow.

Figure 11:
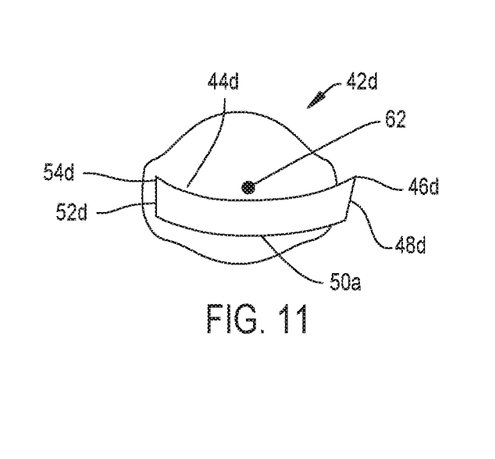
FIG. 11 is a plan view of a fourth alternative bur of this invention looking proximally from the distal end of the bur head.

FIG. 11 illustrates that both the rake surface 44d and clearance surface 50d may have curved profile. In this version of the invention, bur head 42d has a concavo-convex profile wherein the rake surface is the concave surface. In other versions of the invention the clearance surface may be the only concave surface.

Figure 12:
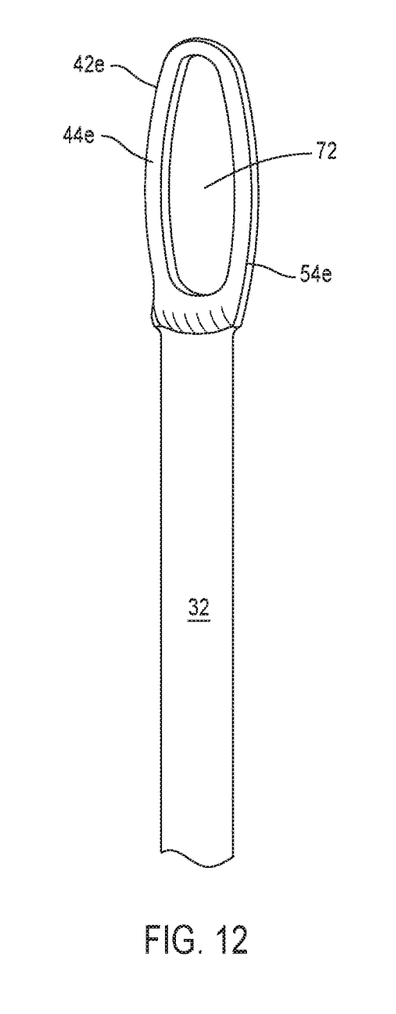
FIG. 12 is a perspective view of fifth alternative bur of this invention.

In the above-described versions of the invention, the bur head is solid. In alternative versions of the invention, the bur head 42e as seen in FIG. 12 is formed with one or more openings 72. One large opening 72 is illustrated seen in FIG. 12. The opening or openings extend from the rake surface to the clearance surface. This opening or openings provide further void space into which the debris formed by the use of the bur can flow. In some versions of the invention, the surface area of this void or plural voids can be 50% of the total area within the perimeter of the bur head 42.

Likewise, the application of this bur is not limited to situations in which tissue with a relatively large water content may adhere to the bur.

Further, in alternative versions of the invention the neck may have shapes different from what has been described. In some versions of the invention, the bur may not even have a neck. In these versions of the invention, the head emerges directly from the shaft.

Figure 2:
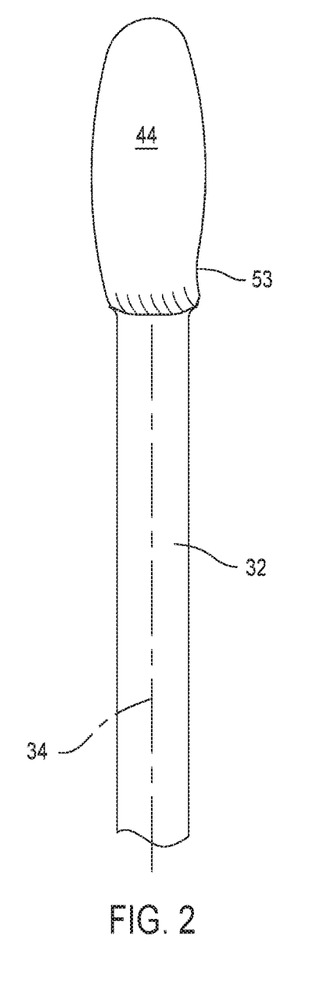
FIG. 2 is a plan view of the bur of FIG. 1 wherein the rake surface is visible.
Figure 3:
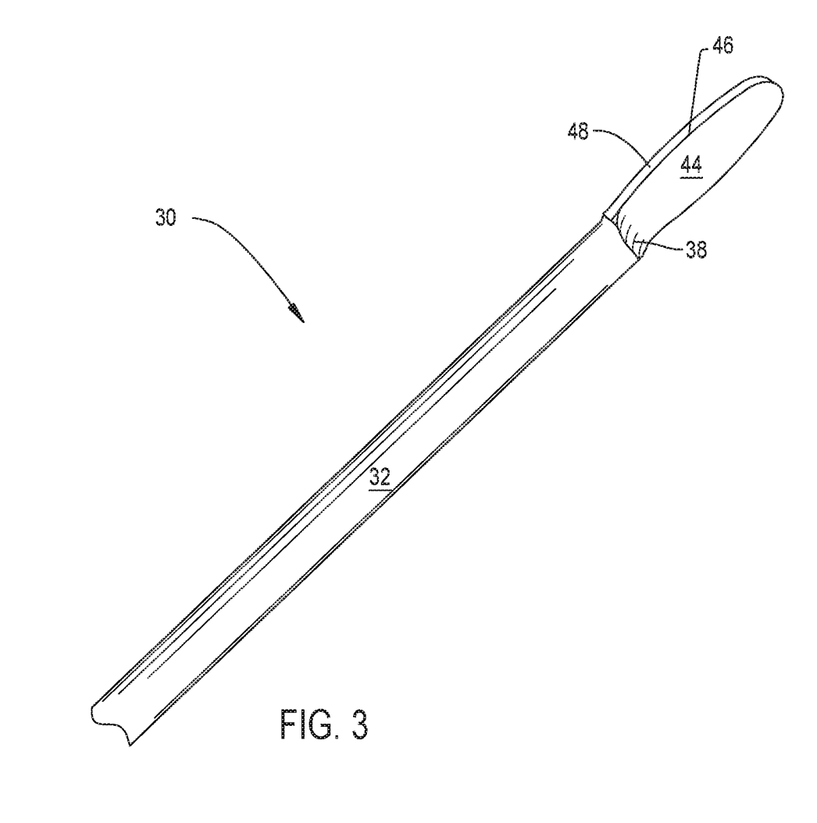
FIG. 3 is a perspective view of the bur of FIG. 1 wherein the clearance surface of the bur is visible.
Figure 4:
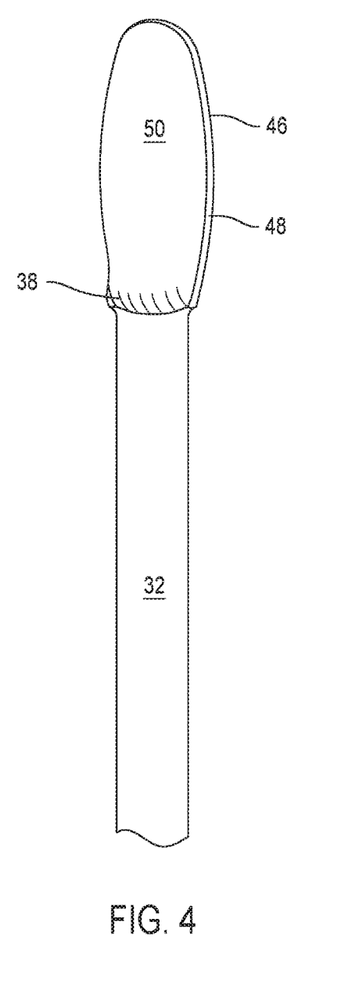
FIG. 4 is a plan view of the bur of FIG. 1 wherein the relief and clearance surfaces are visible.
Figure 13A:
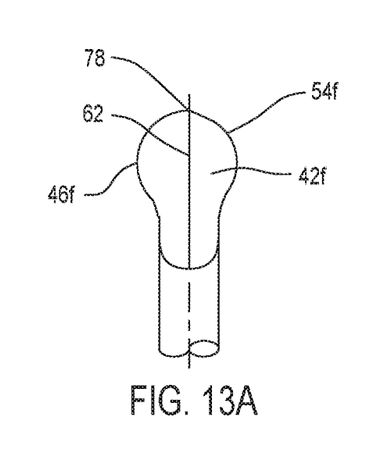
FIGS. 13A-13F are plan views of alternative shapes that are possible for the head of the bur of this invention.

FIGS. 13A through 13E illustrate that there is no requirement that in all versions of the invention the bur head have an elliptical shape similar to the burs of at in FIGS. 2 and 12. FIG. 13A illustrates a bur of this invention with a round head 42f. In this version of the invention, the bur head 42f is generally round. Head 42f is however further formed to have small tip 78 at the most distal end of the head. The bur with head 42f is further formed so the tip 78 is located on the line that is the extension 62 of the longitudinal axis of the shaft 32. A bur with head 42f is further formed so the cutting edge 46f is spaced further from the shaft extension 62 than the recess edge 54f.

Figure 13B:
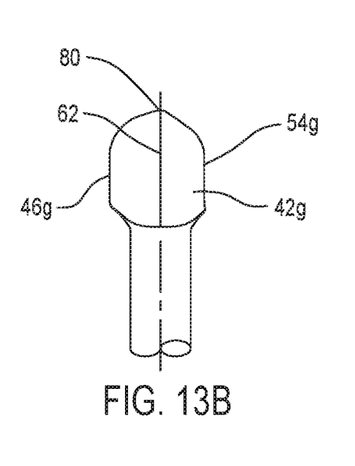

FIG. 13B depicts a bur of this invention with an acorn shaped head 42g. An acorn head 42g is a head wherein proximal to the tip 80, the edges curve proximally rearward around the distal portion of the bur. Proximal to the distal portion of the head 46g, the edges are straight. In the depicted version of the acorn head, the edges are parallel. The bur with head 42g is designed so that the tip 80, is on the shaft extension 62. The bur is further shaped so the cutting edge 46g is spaced further from the shaft extension 62 than the recess edge 54g.

Figure 13C:
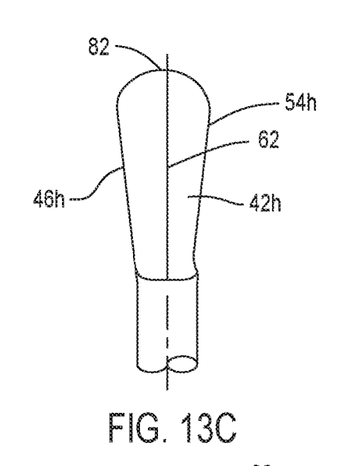

FIG. 13C depicts a bur with a pear-shaped head 42h of this invention. Head 42h thus has a convex distal section. Proximal to the distal section, the opposed edges 46h and 54h of the head 42h are straight and taper inwardly towards each other. In this version of the invention, the distal most point of the head 42h, the point called with identification number 82, is spaced slightly away from the shaft extension 62 and towards the cutting edge 46h. Cutting edge 46h is spaced further from the shaft extension 62 than the recess edge 54h.

Figure 13D:
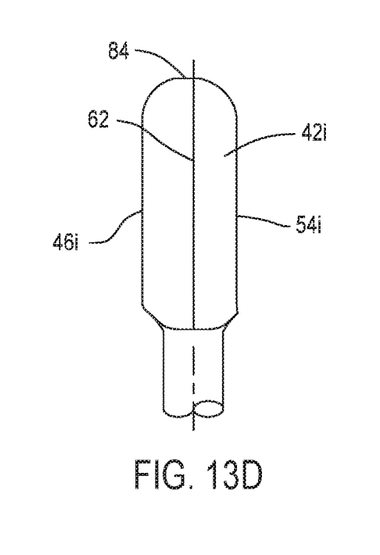

FIG. 13d depicts that a bur of this invention may have a paddle shaped head 42i. Head 42i is similar to the elliptically shaped heads of the burs of FIGS. 2 and 11 of this invention. Head 42i is different in that at the distal end of the bur the distal edge 84 of the head is perpendicular to the shaft extension 62. Also, head 42i is further shaped so that the cutting edge 46i and recess edge 54i are parallel to each other and parallel to the shaft extension 62. Cutting edge 46i is spaced further from shaft extension 62 than recess edge 54i.

Figure 13E:
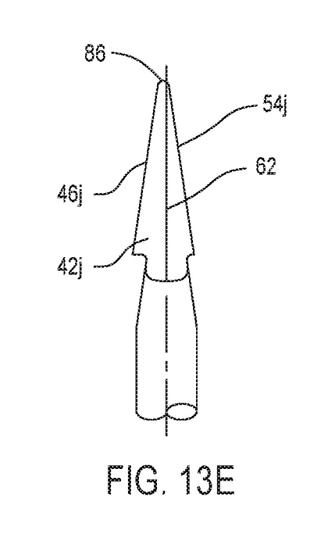

A head 42j of this invention that is arrow shaped is seen in FIG. 13E. Head 13j has a tip 82. The opposed cutting edge and recess edge 46j and 54j, respectively, extend proximally and linearly outwardly away from the tip 82. The bur with head 42j is thus shaped so tip 82 is spaced away from the shaft extension and slightly towards the cutting edge 46j. In this version of the invention edges 46j and 54j are symmetric around the axis through the head that extends through tip 82 and is parallel to the shaft extension 62. Thus in this version of the invention, the cutting edge 46j is spaced further from the shaft extension 62 than the recess edge 54j.

Figure 13F:
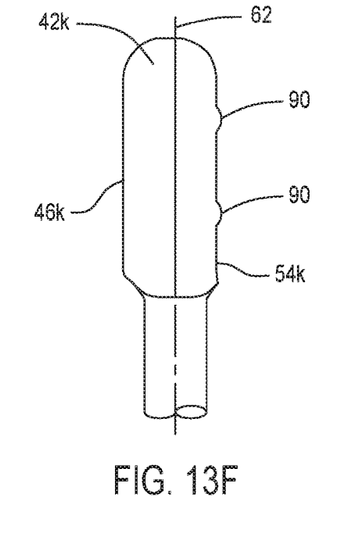

FIG. 13F is an alternative version of the bur of FIG. 13D. Bur head 42k is paddle shaped. Cutting edge 46k is spaced further from the shaft extension 62 than the opposed recess edge 54j. Bur head 42k is further formed to have plural spaced apart ribs 90 that project outwardly from the recess surface, (recess surface not seen in the FIG. 13D). Each rib 90 extends outwardly from the sections of the recess surface distal and proximal to the rib. The bur head 42k is shaped so that the ribs 90 extend outwardly from the shaft extension 62 a distance no greater than the distance the opposed cutting edge 46k extends outwardly from the same line. During the rotation of the bur, ribs 90 hold off the recess surface and recess edge so these portions of the bur head 42k do not strike the tissue against which the bur head is pressed. Since the recess surface and recess edge 54k are spaced away from the tissue, except where the ribs 90 are present, there is a clearance space around these portions of the bur head and the adjacent uncut tissue. This space functions as a void through which newly cut tissue is forced away from the adjacent uncut tissue.

Further, as bur head 42k is pressed against tissue, the cutting edge 46k and flutes 90 are subjected to different resistive forces. It is believed that, since these forces are unequal, repeatedly subjecting to the bur head to these forces reduces the extent to which the application of these forces induces undesirable bur chatter in the bur head.

A bur of this invention may be further shaped so that head has an alternative geometry. An alternative geometry may even be a geometry that includes features of one or more of the above-discussed head shapes. For example, an alternative bur with an arrow head of this invention may be designed so the tip of the head is on the shaft extension. In these versions of the invention, the opposed cutting and recess edges of the head would not be symmetric with respect to the axis running through the tip. Instead, the acute angle between the cutting edge and the portion of the shaft extension 62 along the face of the head is greater than the opposed acute angle between the recess edge and the shaft extension.

The one or more ribs that hold the recess edge off from the tissue against which the bur head is pressed may be incorporated to bur of this invention other than burs having paddle shaped heads.

The stated dimensions and shapes are included to facilitate an understanding of the invention. Unless present in the claims, the dimensions and shapes are therefore not to be interpreted as limiting the invention. For example, in versions of the invention wherein the rake and clearance surfaces of the bur head are parallel, these surfaces may not be parallel along the whole of the bur head. It is within the scope of this invention that these surfaces be parallel along length that is less than the majority, less than 50.1%, of the length of the bur head.

Further, not all features of the above-described versions may be present in all versions of this invention. For example, a bur of this invention may be constructed to have a single flute with a rake surface at least a portion of which that extends from the cutting edge is planar in shape. In these versions of the invention, the cutting edge and recess surface may be spaced the same distance apart from the extension of the longitudinal axis through the shaft. It is believed that in many constructions of this invention of the invention the bur head will be positioned so that the extension of the shaft longitudinal axis does not extend through the head. Thus, in these constructions of the invention the bur head is located so that that extension of the shaft longitudinal axis either extends along the rake surface or is spaced laterally away from the rake surface, and, by extension the whole of the bur head.

Accordingly, it is an object of the appended claims to cover all such variations and modifications the come within the true spirit and scope of the invention.

What is claimed is:

1. A bur for performing a medical/surgical procedure, said bur including:
   an elongated shaft having opposed proximal and distal ends, a longitudinal axis that extends proximally to distally through the shaft, and geometric features adjacent the proximal end of the shaft that facilitate the coupling of the shaft to a surgical handpiece so that the handpiece can rotate the shaft; and
   a head attached to the distal end of the shaft, said head is shaped to define a single cutting flute, said flute having a rake surface with opposed longitudinal sides wherein one side is defined by a cutting edge and the opposed side by a recess edge that extends proximally from the tip and is further shaped so that, in at least one plane perpendicular an extension of the shaft longitudinal axis, the cutting edge is located a first distance from the extension of the shaft longitudinal axis and the recess edge is located a second distance from the extension of the shaft longitudinal axis, the second distance being less than the first distance;
   wherein said head is further formed so as to have a clearance surface that is opposite the rake surface and a majority of the clearance surface is parallel with the rake surface.

2. The bur of claim 1, wherein at least the portion of the rake surface that defines the cutting edge is planar.

3. The bur of claim 1, wherein at least a section of the rake surface that extends between the cutting edge and the recess edge is planar and is in a plane through which the longitudinal axis through the shaft extends or that is parallel to the longitudinal axis through the shaft.

4. The bur of claim 3, wherein the majority of the rake surface is planar between the cutting edge and the recess edge of the flute.

5. The bur of claim 1, wherein said head is further formed so as to have a clearance surface that is opposite the rake surface.

6. The bur of claim 5, wherein the head is further formed so that:
   a relief surface extends from the rake surface, the intersection of the rake surface and the relief surface defining the cutting edge of the flute; and
   the clearance surface extends from an end of the relief surface that is spaced from the rake surface towards the recess edge.

7. The bur of claim 6, wherein at least a portion of the clearance surface is parallel with an opposed portion of the rake surface.

8. The bur of claim 1, wherein:
   said head is further formed so as to have a clearance surface that is opposite the rake surface;
   a relief surface extends from the rake surface and an intersection of the rake surface and the relief surface defines the cutting edge of the flute; and
   a recess surface extends away from the relief surface, the intersection of the rake surface and the recess surface defining the recess edge of the flute; and
   the clearance surface extends from an end of the recess surface that is spaced from the rake surface towards the relief surface.

9. The bur of claim 8, wherein at least one rib extends outwardly from the recess surface of the bur head, said at least one rib extending outwardly from the extension of the shaft longitudinal axis a distance no greater than the distance the cutting edge extends outwardly from the extension of the shaft longitudinal axis.

10. The bur of claim 1, wherein:
    said head is further formed so as to have a clearance surface that is opposite the rake surface and the clearance surface extends to the end of the rake surface spaced away from the cutting edge so that an intersection of the rake surface and the clearance surface form the recess edge.

11. The bur of claim 1, wherein:
    said head is further formed to have a clearance surface that is opposite the rake surface; and
    said head is located on said shaft so that the rake surface and the clearance surface are located on opposed sides of the extension of the shaft longitudinal axis.

12. The bur of claim 1, wherein said head is located relative to the shaft so that an extension of said shaft longitudinal axis of the shaft extends along the rake surface.

13. The bur of claim 1, wherein said head is further formed so that the cutting edge and the recess edge are located on opposed sides of the extension of the shaft longitudinal axis.

14. The bur of claim 1, wherein said head has a concaveoconvex profile such that rake surface has a concave profile and the opposed surface has a convex profile.

15. The bur of claim 1, wherein along the entire length of said head the cutting edge is spaced further from the longitudinal axis of the shaft than the recess edge.

16. The bur of claim 1, wherein said head has a shape selected from the group consisting of: elliptically shaped; round; acorn shaped; pear shaped; paddle shaped; or arrow shaped.

17. The bur of claim 1, wherein the geometric features adjacent the proximal end of the shaft that facilitate the coupling of the shaft to a surgical handpiece are from the group consisting of: an indentation formed in the shaft; and the shaft being dimensioned to be held by chuck jaws.

18. The bur of claim 1, wherein the head is shaped so that the tip is a distal edge that is perpendicular to the extension of the shaft longitudinal axis.

19. The bur of claim 1, wherein the head is arrow shaped so that, as the cutting edge tip and recess edge extend distally away from the shaft, the cutting edge and the recess edge extend linearly inwardly towards the tip.

20. The bur of claim 1, wherein the head is located relative to the shaft so that the tip is spaced away from the extension of the shaft longitudinal axis.

21. The bur of claim 1, wherein the head is located relative to the shaft so the tip is located on the extension of the longitudinal axis of the shaft.

22. The bur of claim 1, wherein the head is further shaped so that, as the recess edge extends proximally from the tip, the recess edge curves outwardly as to have a convex shape.

23. The bur of claim 1, wherein the shaft coupling features are surfaces that are recessed relative to the outer surface of the shaft.

\* \* \* \* \*